United States Patent
Tsukuda et al.

(10) Patent No.: US 12,112,473 B2
(45) Date of Patent: *Oct. 8, 2024

(54) IMAGE PROCESSING APPARATUS, IMAGE PROCESSING METHOD, AND NON-TRANSITORY COMPUTER-READABLE STORAGE MEDIUM THAT USE A PLURALITY OF CAPTURED RADIATION IMAGES TO OBTAIN, BY SEQUENTIAL APPROXIMATION SOLUTION BY ITERATIVE CALCULATION, AN OUTPUT IMAGE

(71) Applicant: CANON KUBUSHIKI KAISHA, Tokyo (JP)

(72) Inventors: Akira Tsukuda, Tokyo (JP); Atsushi Iwashita, Tokyo (JP); Sota Torii, Tokyo (JP); Takeshi Noda, Kanagawa (JP); Kosuke Terui, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 399 days.

This patent is subject to a terminal disclaimer.

(21) Appl. No.: 17/526,697

(22) Filed: Nov. 15, 2021

(65) Prior Publication Data
US 2022/0076415 A1   Mar. 10, 2022

Related U.S. Application Data

(63) Continuation of application No. PCT/JP2020/014095, filed on Mar. 27, 2020.

(30) Foreign Application Priority Data

May 30, 2019   (JP) .................................. 2019-101484

(51) Int. Cl.
  *G06T 7/00*   (2017.01)

(52) U.S. Cl.
  CPC .. *G06T 7/0012* (2013.01); *G06T 2207/10116* (2013.01); *G06T 2207/20076* (2013.01)

(58) Field of Classification Search
  CPC ............ A61B 6/00; G06T 2207/10116; G06T 2207/20076; G06T 2207/30008; G06T 5/70; G06T 7/0012
  See application file for complete search history.

(56) References Cited

U.S. PATENT DOCUMENTS 5,970,424 A * 10/1999 Kaffka ................. G01N 21/359
                                                                    702/30
9,662,081 B2     5/2017 Maeda et al.
(Continued)

FOREIGN PATENT DOCUMENTS

JP    H03-285475 A    12/1991
JP    2011-156302 A    8/2011
(Continued)

OTHER PUBLICATIONS

Ewald Roessl, "Sensitivity of Photon-Counting Based◆◆-Edge Imaging in X-ray Computed Tomography," Apr. 15, 2011, IEEE Transactions On Medical Imaging, vol. 30, No. 9, Sep. 2011, pp. 1678-1688.*

(Continued)

*Primary Examiner* — Omar S Ismail
(74) *Attorney, Agent, or Firm* — Venable LLP (57) ABSTRACT

An image processing apparatus includes a planar distribution obtaining unit configured, using a plurality of radiation images captured using different radiation energies as input images, to obtain, by a sequential approximation solution by an iterative calculation, an output image representing a planar distribution for a substance contained in the input image. Based on a likelihood and a prior probability using one of a pixel value of a pixel of interest or a pixel value of a peripheral pixel as an input, the planar distribution obtain- (Continued)

ing unit decides the output image such that a probability that an output is a value of the planar distribution when an input is the input image that is maximized.

19 Claims, 4 Drawing Sheets

(56) References Cited

U.S. PATENT DOCUMENTS

| | | | | |
|---|---|---|---|---|
| 2003/0052169 | A1* | 3/2003 | Tsikos | G06V 20/62 235/454 |
| 2003/0150917 | A1* | 8/2003 | Tsikos | G02B 26/105 235/454 |
| 2003/0156684 | A1* | 8/2003 | Fessler | A61B 6/032 378/210 |
| 2007/0012777 | A1* | 1/2007 | Tsikos | G02B 26/10 235/454 |
| 2010/0312072 | A1* | 12/2010 | Breskin | A61B 6/485 600/300 |
| 2011/0103692 | A1* | 5/2011 | Williams | G06T 5/94 382/190 |
| 2013/0156285 | A1* | 6/2013 | Hayashida | G06T 5/70 382/132 |
| 2016/0120493 | A1* | 5/2016 | Maeda | A61B 6/5205 382/131 |
| 2016/0292851 | A1* | 10/2016 | Hamauzu | G06T 5/70 |
| 2017/0003416 | A1* | 1/2017 | Zhang | G01V 8/02 |
| 2017/0294034 | A1* | 10/2017 | Zhou | G06T 11/008 |
| 2017/0323481 | A1* | 11/2017 | Tran | H04N 23/611 |
| 2018/0308233 | A1* | 10/2018 | Machida | A61B 6/505 |
| 2019/0060602 | A1* | 2/2019 | Tran | G16H 20/30 |
| 2020/0118250 | A1* | 4/2020 | Takahama | H04N 25/60 |
| 2020/0151880 | A1* | 5/2020 | Stayman | G16H 50/50 |
| 2020/0020575 | A1 | 7/2020 | Iwashita et al. | |
| 2020/0321188 | A1* | 10/2020 | Hujsak | G01N 23/2251 |
| 2021/0150686 | A1* | 5/2021 | Shimada | G06T 5/50 |
| 2021/0173096 | A1* | 6/2021 | Petrak | G06T 11/006 |
| 2023/0097849 | A1* | 3/2023 | Takahashi | G06V 10/70 382/131 |

FOREIGN PATENT DOCUMENTS

| | | |
|---|---|---|
| JP | 2019068953 A | 5/2019 |
| WO | 2014185078 A1 | 11/2014 |
| WO | 2018105493 A1 | 6/2018 |

OTHER PUBLICATIONS

Jia Hao, "A novel image optimization method for dual-energy computed tomography," May 6, 2013, Nuclear Instruments and Methods in Physics Research A 722 ( 2013) , pp. 34-40.*

Catherine Lemmens, "Suppression of Metal Artifacts in CT Using a Reconstruction Procedure That Combines MAP and Projection Completion,"Jan. 30, 2009, IEEE Transactions On Medical Imaging, vol. 28, No. 2, Feb. 2009, pp. 250-259.*

Yong Long, "Multi-Material Decomposition Using Statistical Image Reconstruction for Spectral CT,"Jul. 30, 2014, IEEE Transactions On Medical Imaging, vol. 33, No. 8, Aug. 2014, pp. 1614-1622.*

Ewald Roessl, "Sensitivity of Photon-Counting Based Edge Imaging in X-ray Computed Tomography,"Apr. 15, 2011, IEEE Transactions On Medical Imaging, vol. 30, No. 9, Sep. 2011, pp. 1678-1688.*

Ke Li, Statistical model based iterative reconstruction (MBIR) in clinical CT systems: Experimental assessment of noise performance, Mar. 13, 2014, Med. Phys. 41 (4), Apr. 2014, pp. 041906-1-041906-13.*

Drosoula Giantsoudi et al., "Metal artifacts in computed tomography for radiation therapy planning: dosimetric effects and impact of metal artifact reduction,"Mar. 21, 2017, Phys. Med. Biol. 62 (2017), pp. R49-R69.*

International Search Report issued Jun. 9, 2020 in International Appln No. PCT/JP2020/014095.

Lemmens et al., "Suppression of Metal Artifacts in CT Using a Reconstruction Procedure That Combines MAP and Projection Completion," IEEE Transactions on Medical Imaging, vol. 28, No. 2, pp. 250-260, Jan. 30, 2009.

* cited by examiner

IMAGE PROCESSING APPARATUS, IMAGE PROCESSING METHOD, AND NON-TRANSITORY COMPUTER-READABLE STORAGE MEDIUM THAT USE A PLURALITY OF CAPTURED RADIATION IMAGES TO OBTAIN, BY SEQUENTIAL APPROXIMATION SOLUTION BY ITERATIVE CALCULATION, AN OUTPUT IMAGE

CROSS-REFERENCE TO RELATED APPLICATIONS

This application is a Continuation of International Patent Application No. PCT/JP2020/014095, filed Mar. 27, 2020, which claims the benefit of Japanese Patent Application No. 2019-101484, filed May 30, 2019, both of which are hereby incorporated by reference herein in their entirety.

BACKGROUND OF THE INVENTION

Field of the Invention

The present invention relates to an image processing apparatus, an image processing method, and a non-transitory computer-readable storage medium.

Background Art

In recent years, by a spectral imaging technique that is an imaging technique using energy information of radiation, thickness images of a plurality of substances can be obtained from a plurality of different radiation energy images, or an image of a surface density and an effective atomic number image can be obtained. Assuming that radiation transmitted through a substance attenuates as an exponential function of a thickness, or the like, such a thickness image, a surface density image, or an effective atomic number image (an example of "a planar distribution concerning a substance") can be obtained by backward calculation from the pixel values of transmitted radiation.

Japanese Patent Laid-Open No. H3-285475 discloses a technique of smoothing an image of a soft tissue and subtracting the image from an accumulated image, thereby improving the image quality of a bone part image.

However, in the estimation operation of a planar distribution concerning a substance, system noise or quantum noise derived from radiation propagates in a calculation process, and an output image may include the noise. In the technique of Japanese Patent Laid-Open No. H3-285475, the estimation operation of a planar distribution is performed using four simple arithmetic operations. If the dose of radiation is low, noise cannot completely be removed, and an image may be unclear due to smoothing.

The present invention provides an image processing technique capable of reducing probabilistically distributed noise and obtaining an image of a higher image quality.

SUMMARY OF THE INVENTION

According to an aspect, the present invention provides a planar distribution obtaining unit configured, using a plurality of radiation images captured using different radiation energies as input images, to obtain an output image representing a planar distribution for a substance contained in the input image, wherein, based on a likelihood and a prior probability using one of a pixel value of a pixel of interest or a pixel value of a peripheral pixel as an input, the planar distribution obtaining unit decides the output image such that a probability that an output is a value of the planar distribution when an input is the input image is maximized.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Hereafter, embodiments will be described in detail with reference to the attached drawings. Note, the following embodiments are not intended to limit the scope of the claimed invention. Multiple features are described in the embodiments, but a limitation is not made to an invention that requires all such features, and multiple such features may be combined as appropriate. Furthermore, in the attached drawings, the same reference numerals are given to the same or similar configurations, and a redundant description thereof is omitted.

In the following embodiment and claims, radiation includes a-rays, p-rays, y-rays, and various kinds of particle beams in addition to X-rays.

Figure 1:
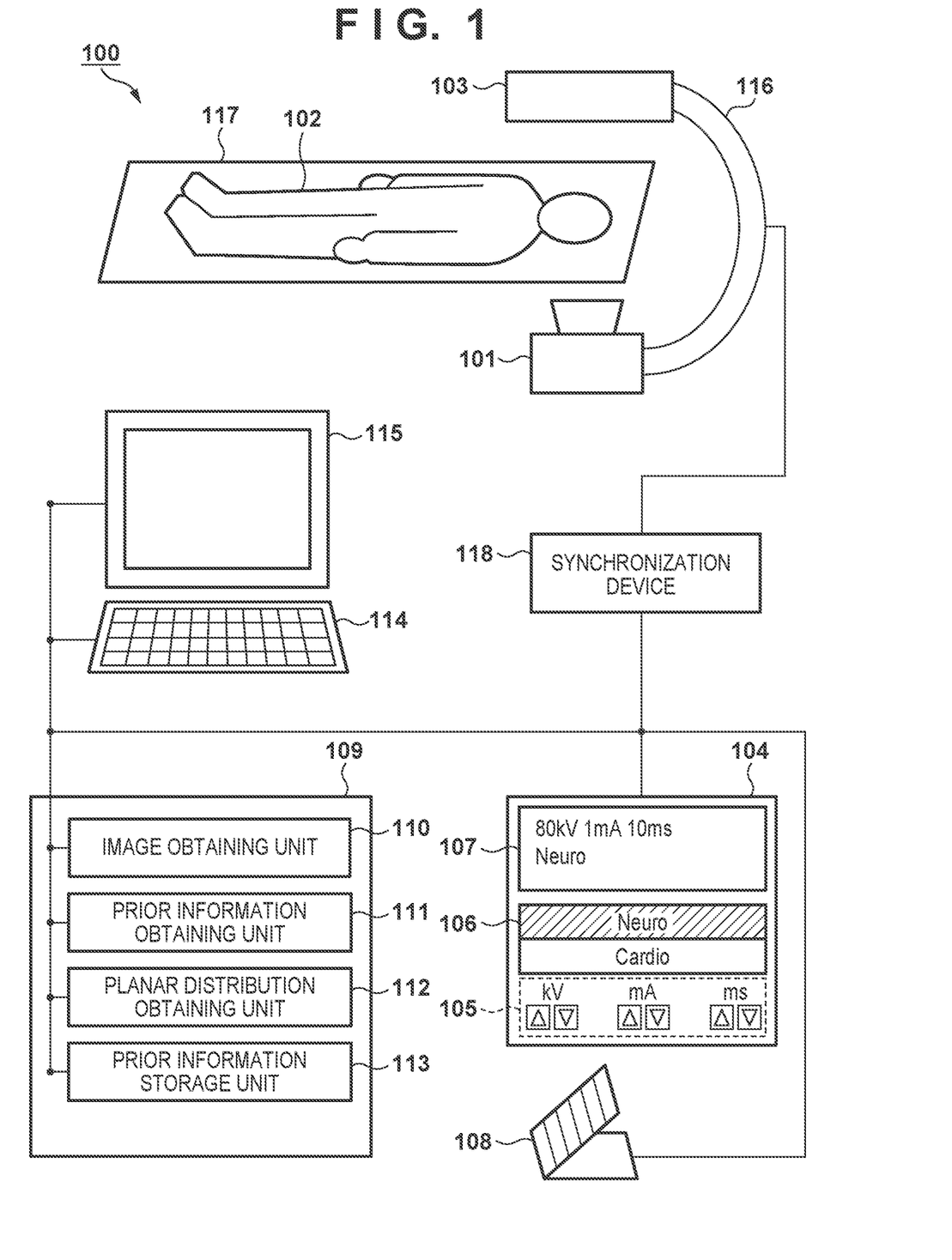
FIG. 1 is a view showing an example of the configuration of a radiation imaging apparatus according to the embodiment.

FIG. 1 is a view showing an example of the configuration of a radiation imaging apparatus 100 according to the embodiment of the present invention. The radiation imaging apparatus 100 includes a radiation tube 101, an FPD 103 (Flat Panel Detector (radiation detection unit)), a computer 109 (image processing apparatus), an operation panel 104, a synchronization device 118, and an irradiation instruction unit 108.

The radiation tube 101 generates radiation based on a radiation irradiation instruction signal transmitted from the synchronization device 118 and irradiates a subject 102 with the radiation. The radiation tube 101 may be provided with a filter configured to remove low-energy radiation. When the subject 102 is irradiated with the radiation from the radiation tube 101, the radiation passes through the subject 102 and enters the FPD 103.

The FPD 103 includes a phosphor that converts radiation into visible light, an imaging element (a plurality of elements exist, and one element corresponds to one pixel) that converts the visible light into charges or a voltage, an image forming unit that further converts the converted voltage into an image of a digital value, and an image correction unit that performs correction (offset correction, gain correction, and defect correction) for the image. In the imaging element, pixels configured to output signals according to incident light are arranged in an array (two-dimensional region). The image forming unit of each pixel converts the radiation converted into the visible light by the phosphor into an electrical signal and outputs the signal as an image signal. Note that this embodiment can also be applied to an FPD of a type for directly converting radiation into a voltage, for example, an FPD using cadmium telluride (CdTe) or amorphous selenium (a-Se). The FPD 103 accumulates charges based on the image signal to obtain a radiation image, and outputs the radiation image to the computer 109.

The operation panel 104 can designate irradiation conditions of radiation to be emitted from the radiation tube 101. The operation panel 104 includes a condition designation unit 105, an imaging part designation unit 106, and a condition display unit 107. The condition designation unit 105 can designate a tube voltage, a tube current, and an irradiation time based on operation inputs from an operator via operation portions such as buttons. The operation panel 104 holds an image quality adjusting unit (a dial, or the like) configured to adjust image quality. By operating the dial, the operator can set image quality that makes it easy for an image confirmer, such as a doctor, to confirm a radiation image.

In the imaging part designation unit 106, an imaging part and radiation irradiation conditions are associated in advance. When the operator designates an imaging part of a subject, the imaging part designation unit 106 can invoke and set radiation irradiation conditions associated with the designated imaging part. The condition display unit 107 is configured to display the designated radiation irradiation conditions.

The irradiation instruction unit 108 is a foot pedal. When the operator steps on the pedal, an irradiation instruction signal is input to the synchronization device 118, and the radiation tube 101 can emit radiation under the control of the synchronization device 118.

The image (radiation image) output from the FPD 103 is transferred to the computer 109. The computer 109 can function as an image processing apparatus for processing the radiation image obtained from the FPD 103, and includes, as functional components, an image obtaining unit 110 that obtains an image (radiation image) from the FPD 103, a prior information obtaining unit 111, a planar distribution obtaining unit 112, and a prior information storage unit 113. These functional components can be formed by, for example, hardware such as the central processing unit (CPU) of the computer 109, a main storage device, a storage device such as a hard disk, a graphic processing unit for high-speed calculation, and a LAN (Local Area Network) adapter (none are shown).

Each function can be implemented as software. For example, the function of each unit can be constituted using the central processing unit and a program loaded from the storage device. Units that provide the same function may be constituted by an integrated circuit (similar electric circuit). Note that the image correction unit mounted in the FPD 103 may be provided in the computer 109. Also, in place of the operation panel 104, radiation irradiation conditions may be stored in the computer 109 in advance. In this case, when designating the radiation irradiation conditions on the operation panel 104, the operation panel 104 reads out the stored irradiation conditions from the computer 109 and sets these.

The image obtaining unit 110 obtains an image (radiation image) from the FPD 103. Also, the prior information obtaining unit 111 includes, as prior information, for example, information of a probability distribution concerning radiation (for example, information such as the function of a Poisson distribution or normal distribution or an average value or a standard deviation as a parameter of a Poisson distribution or normal distribution), tube information (information including a tube voltage, a tube current, an irradiation time, and the presence/absence of a radiation filter), information concerning the FPD 103 (an accumulation time, and the like), imaging part information (for example, a part such as the chest or head of a subject), subject information (the identification number, name, sex, age, height, weight, and the like, of a subject input by an input device 114), contrast medium information (the type, density, and concentration, and the like, of a contrast medium), information of a C-arm 116 (the material, position, angle, and the like), and information of a gantry 117 (the position of the gantry, and the like).

The planar distribution obtaining unit 112 receives, as an input image, a plurality of radiation images captured using different radiation energies, and obtains an output image representing a planar distribution for a substance contained in the input image. A calculation process by the planar distribution obtaining unit 112 will be described later.

The input device 114 connected to the computer 109 functions as a user interface that inputs an instruction to the computer 109 or the FPD 103. The input device 114 can be formed by, for example, the keyboard of the computer 109. The operator can input imaging part information or subject information using the input device 114. In addition to input by the input device 114, the imaging part information or subject information may be input from, for example, an external apparatus via a network and a LAN adapter implemented in the computer 109.

In addition, a display device 115 connected to the computer 109 can display a radiation image (digital image) that the computer 109 has received from the FPD 103, or an image (image that has undergone image processing) output from the computer 109. In particular, if a color display is used as the display device 115, a planar distribution concerning a substance can be expressed as colors, and image diagnosis performance can be improved.

Some of the functions of the operation panel 104 may be provided in the input device 114 and the display device 115. For example, the radiation irradiation condition input operation that is performed via the condition designation unit 105 or the imaging part designation unit 106 of the operation panel 104 may be performed by the input device 114, and display of an input radiation irradiation condition such as a tube voltage may be done, not by the condition display unit 107, but by the display device 115.

The synchronization device 118 is connected to the radiation tube 101, the FPD 103, the operation panel 104, the irradiation instruction unit 108, and the computer 109, and determines, based on the state of the FPD 103, the pressed state of the irradiation instruction unit 108, and the processing state of the computer 109, whether radiation irradiation is possible. The synchronization device 118 functions as an irradiation control unit, and controls radiation irradiation and imaging based on a decided timing.

The procedure of an imaging process according to the embodiment of the present invention will be described with reference to the flowchart of FIG. 2. In step S201, the operator of the radiation imaging apparatus 100 inputs radiation irradiation conditions. The input of the radiation irradiation conditions can be performed via, for example, the condition designation unit 105 or the imaging part designation unit 106 of the operation panel 104. Information such as the identification number of the subject is input together via the input device 114.

In step S202, the operator instructs radiation irradiation via the irradiation instruction unit 108. After that, in step S203, the synchronization device 118 determines, based on the states of the radiation tube 101, the FPD 103, the operation panel 104, the irradiation instruction unit 108, and the computer 109, whether irradiation is possible. If irradiation is impossible (NO in step S203), in step S204, the synchronization device 118 causes the display device 115 to display a warning. On the other hand, if the synchronization device 118 determines that irradiation is possible in step S203 (YES in step S203), the process advances to step S205.

In step S205, the prior information obtaining unit 111 obtains, as prior information, information of a probability distribution concerning radiation, tube information, information concerning the FPD 103, imaging part information, subject information, and the like. At this time, the number of images to be obtained is decided in accordance with information such as the number of substances to be identified (for example, if substance separation is to be performed by two energies of different energy levels (high energy and low energy), the number of images to be obtained is two). The prior information obtaining unit 111 then notifies the synchronization device 118 of the decided number of image to be obtained, information (accumulation time and the like) in the FPD 103, and the like.

In step S206, the synchronization device 118 generates a radiation irradiation instruction signal based on the information obtained from the prior information obtaining unit 111, and transmits the radiation irradiation instruction signal to the radiation tube 101 and the FPD 103. This controls radiation irradiation by the radiation tube 101 and image obtaining by the FPD 103. The FPD 103 captures a plurality of radiation images (for example, a low-energy radiation image and a high-energy radiation image) captured using different radiation energy levels.

When the necessary number of images to be obtained are obtained by the FPD 103, imaging is ended in step S207. If imaging is ended in step S207, the image obtaining unit 110 obtains the images (radiation images) from the FPD 103. That is, the image obtaining unit 110 obtains the plurality of radiation images (the low-energy radiation image and the high-energy radiation image) captured using different radiation energy levels.

In step S208, the planar distribution obtaining unit 112 calculates a planar distribution concerning a substance based on the prior information such as the information of the probability distribution concerning radiation obtained in step S205 and the images obtained in step S206. A detailed planar distribution calculation process will be described later.

In step S209, the CPU of the computer 109 stores the calculation result of the planar distribution in the storage device in the computer 109. In addition, the CPU displays the calculation result of the planar distribution on the display device 115. The CPU can perform display control to display, on the display device 115 in colors, an image (substance identification image) that makes, for example, the calculation result of the planar distribution of the thickness, the effective atomic number, the surface density, or the like, of a separated substance correspond to colors of visible light.

[0037] (Planar Distribution Calculation Process) Next, the calculation processing method of a planar distribution concerning a substance in step S208 will be described in detail. Here, as an example of planar distribution calculation concerning a substance, a process of outputting an image (substance separation image) representing the distribution of thicknesses of each substance from images of two colors (two types of images including a high-energy radiation image and a low-energy radiation image) will be described. The planar distribution calculation process can similarly be applied to images of three or more colors.

Radiation distribution information temporarily stored in the FPD 103 can be read out after execution of sampling hold. The image obtaining unit 110 executes read of radiation distribution information $(X_L)$ and radiation distribution information $(X_L+X_H)$ from the FPD 103 at different timings. The image obtaining unit 110 can obtain radiation distribution information $(X_H)$ by subtracting the radiation distribution information $(X_L)$ from the radiation distribution information $(X_L+X_H)$. Here, the low-energy radiation distribution information $(X_L)$ is an image by low-energy radiation (low-energy radiation image), and the high-energy radiation distribution information $(X_H)$ is an image by high-energy radiation (high-energy radiation image).

The planar distribution obtaining unit 112 obtains a substance characteristic image concerning a substance contained in a plurality of radiation images captured using different radiation energies. Using a plurality of radiation images obtained by one radiation irradiation, the planar distribution obtaining unit 112 can obtain a substance characteristic image such as a substance separation image or a substance identification image.

Here, the substance separation image is an image that separates a plurality of substances contained in a plurality of radiation images (a low-energy radiation image and a high-energy radiation image), and means an image obtained by, in a case in which a subject is represented by two or more specific substances, separating the image into two or more images formed by the thicknesses of the substances.

In addition, the substance identification image is an image representing the distribution of the effective atomic number and the surface density of a substance contained in a plurality of radiation images (a low-energy radiation image and a high-energy radiation image), and means an image obtained by, in a case in which a subject is represented by one specific substance, decomposing the image into the distribution of the effective atomic number and the surface density of the substance.

As for a planar distribution concerning a substance, an image is divided into two types of images, including an image (thickness image) representing the distribution of the thickness of a separated substance, and an image (effective atomic number image) representing the distribution of an effective atomic number concerning a specific substance and an image (surface density) representing the distribution of a surface density. Even in a case in which an image is divided into three or more images including an effective atomic number image, a surface density image, and a thickness image, the planar distribution calculation process can similarly be applied.

As input images, two radiation images (a low-energy radiation image and a high-energy radiation image) are defined as $I=(I(E_1), I(E_2))$ as images of different radiation energies. Here, $E_1$ and $E_2$ represent radiation energies. Also, as output images, substance thickness images are defined as $f(d)=(d_1, d_2)$. The relationship between the input image $(I)$ and the output image $(f(d))$ in the absence of noise can be represented by:

$$I=f(d) \qquad (1)$$

In an actually obtained image, if quantum noise derived from the statistical characteristic of radiation or a system noise derived from electrical noise of a detector exists, in the relationship between the input image (I) and the output image (f(d)), the relationship of equation (1) does not necessarily hold in some cases. In general, letting n be noise, in the relationship between the input image (I) and the output image (f(d)) and the noise, the noise n is expressed as the difference between the input image (I) and the output image (f(d)).

$$n = I - f(d) \quad (2)$$

The probability distribution that the noise n complies with can be considered as a probability that the image is I when the thickness of the substance is d. Hence, the probability distribution that the noise n complies with can be represented by p(I|d).

A planar distribution concerning a substance to be obtained is the planar distribution of a thickness d of each substance that can be contained in the input image when the input image is I (=(I($E_1$), I($E_2$))). As for the thickness d of each substance, it can be considered that the thickness to be obtained is the thickness d of the substance whose probability is maximum when the input image is I. That is, the thickness is the thickness d of the substance that satisfies equation (3) below. The planar distribution obtaining unit 112 decides the output image such that when the input is the input image (I), the probability (posterior probability) that the output is the value (d) of the planar distribution is maximized.

$$\max_d p_{post}(d \mid I) \quad (3)$$

It may be considered that the thickness of the substance to be obtained is the thickness d of the substance for which the logarithm of the probability distribution is maximum. In this case, the form of the equation can be represented by equation (4) or equation (5) below.

$$\max_d \log p_{post}(d \mid I) \quad (4)$$

$$\min_d - \log p_{post}(d \mid I) \quad (5)$$

When equation (5) is rewritten using the Bayes' theorem, it can be rewritten as equation (6) below. The probability (posterior probability) can be obtained based on a likelihood and the prior probability. That is, the planar distribution obtaining unit 112 decides the output image based on the likelihood and the prior probability using, as the input, the pixel value of a pixel of interest or the pixel value of a peripheral pixel, such that when the input is the input image (I), the probability (posterior probability) that the output is the value (d) of the planar distribution is maximized. Here, the likelihood indicates the probability that an image corresponding to an input becomes an input image when an input value is a value (the thickness d of a substance) of the planar distribution.

$$\min_d - \log p_{post}(d \mid I) = \min_d \{-\log p(I/d) - \log p_{prior}(d)\} \quad (6)$$

Here, in equation (6), log p(I|d) is a term called a likelihood, and log $p_{prior}(d)$ is a term called a prior probability. When the form of the term of prior probability is changed, a probability reflecting a variety of prior information can be calculated. The prior probability has an effect of making the solution of equation (6) more robust, and is sometimes called a regularization term.

There exist several methods of obtaining equation (6). If the extreme value is the minimum value, equation (6) can be obtained by, for example, the steepest descent method. Other than this, another generally known method such as the Newton's method can be used. If the steepest descent method is applied, a sequential approximation solution of $d_{n+1}$ is obtained in the form of equation (7) below, and the solution of equation (6) can be obtained from the obtained sequential approximation solution. The planar distribution obtaining unit 112 can obtain the output image by the sequential approximation solution by an iterative calculation.

$$d_{n+1} = d_n - \alpha_n \times \text{grad}(-\log p(I|d) - \log p_{prior}(d_n)) \quad (7)$$

In equation (7), $d_n$ is the thickness of the substance obtained by the nth iteration, a is a coefficient representing the speed of iteration, and grad is a symbol representing the differential (gradient) of a vector. That is, the thickness $d_{n+1}$ of the substance whose probability is maximum when the input image is I can sequentially be obtained by repeating iteration as shown by equation (7).

Figure 2:
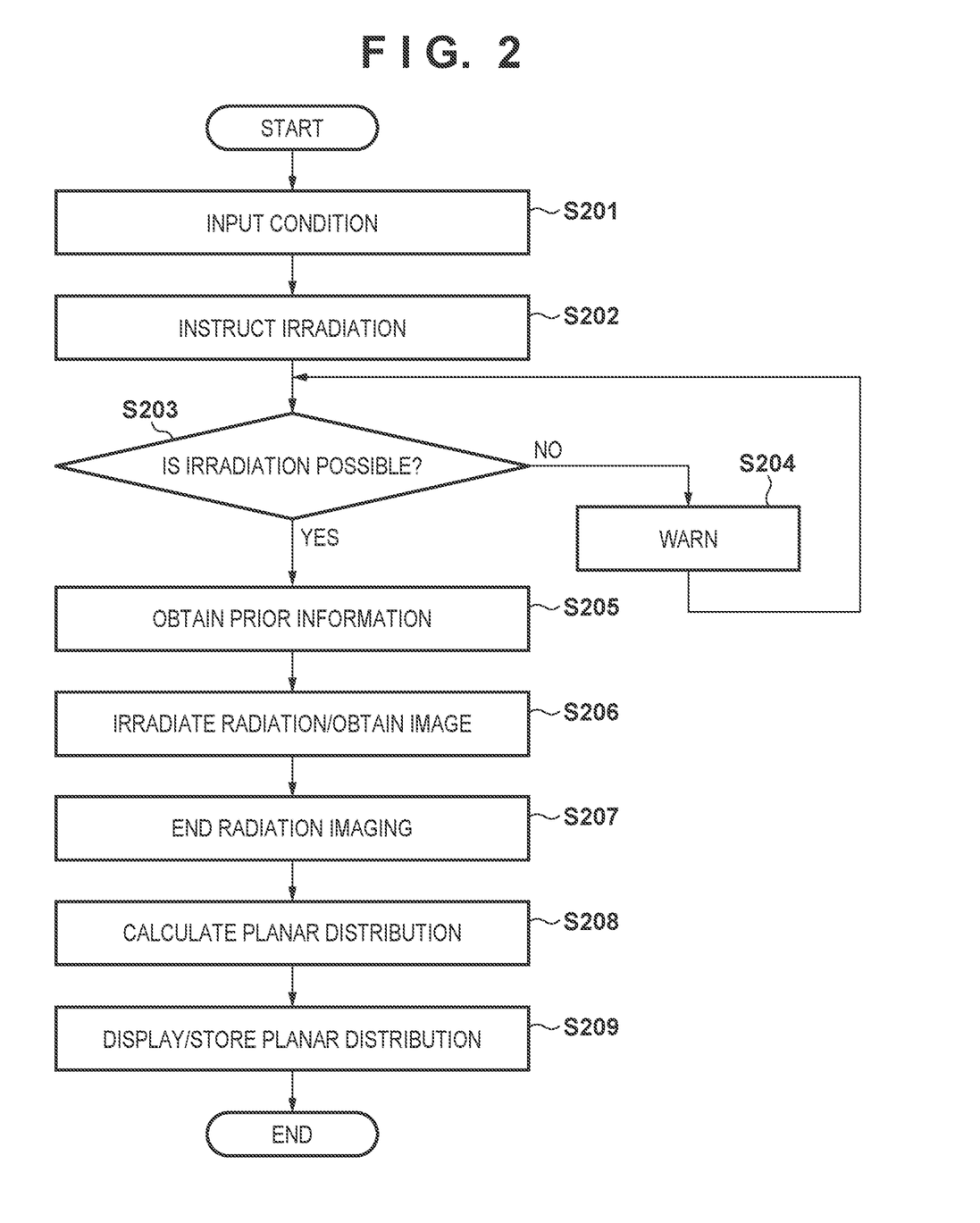
FIG. 2 is a flowchart for explaining the procedure of an imaging process according to the embodiment.
Figure 3:
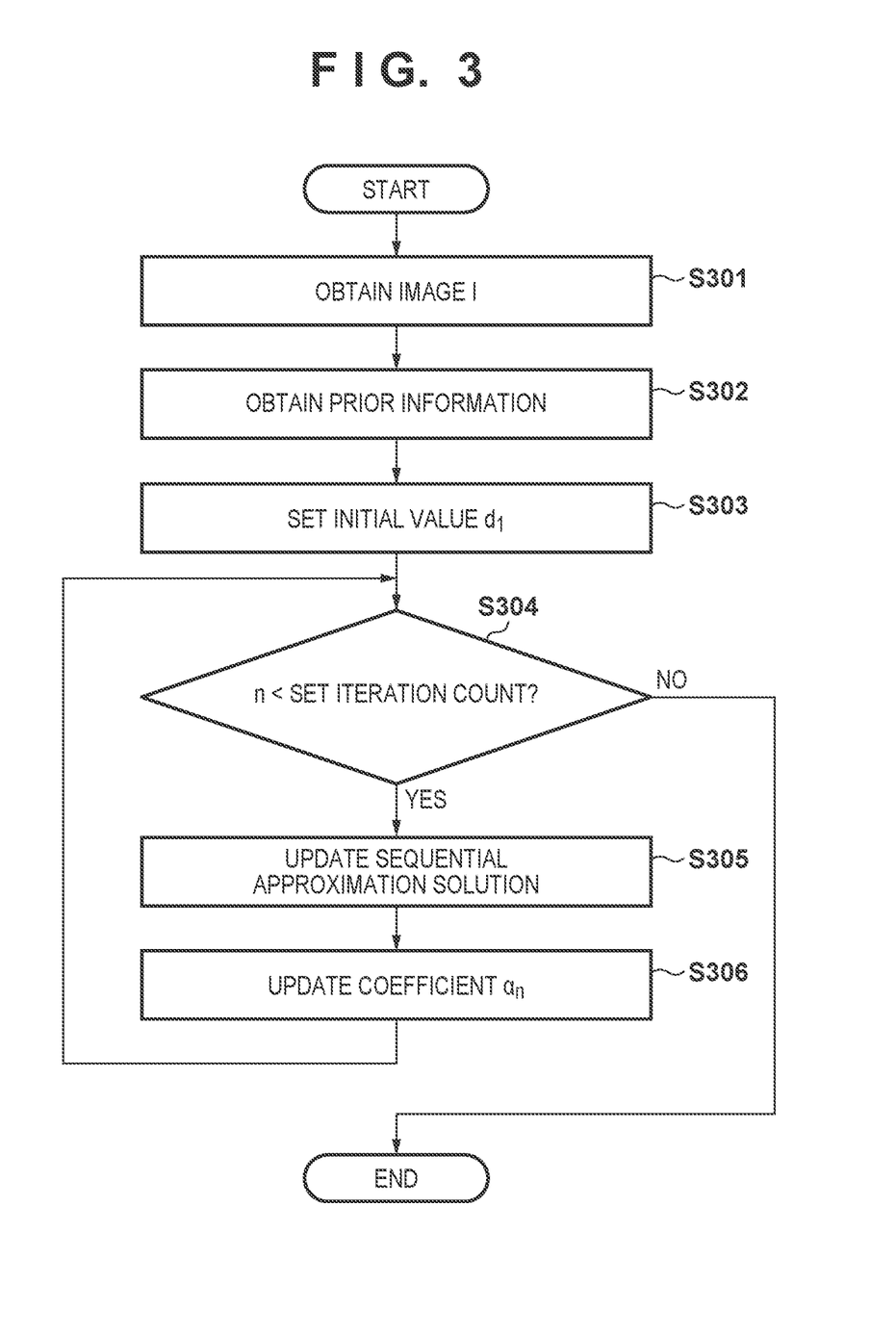
FIG. 3 is a flowchart for explaining the procedure of a process of obtaining the planar distribution of a substance.

FIG. 3 is a flowchart for explaining the procedure of a detailed process (a process of obtaining the planar distribution of a substance) of step S208 in FIG. 2. In step S301, the image obtaining unit 110 obtains an image (radiation image) from the FPD 103. When imaging is ended in step S207 of FIG. 2, the image obtaining unit 110 obtains a plurality of radiation images (a low-energy radiation image and a high-energy radiation image) captured using different radiation energy levels. The two radiation images, that is, the low-energy radiation image and the high-energy radiation image are the input images I in step S301.

In step S302, the prior information obtaining unit 111 obtains prior information such as the information of the probability distribution concerning radiation obtained in step S205.

In step S303, the planar distribution obtaining unit 112 sets an initial value ($d_1$) before the iterative calculation is performed. The set initial value can be the planar distribution (the thickness of the substance) when, for example, noise is assumed to be absent in the system. Since the relationship between the input image (I) and the output image (f(d)) concerning the thickness d of the substance in the absence of noise can be represented by equation (1), the initial value $d_1$ of the planar distribution (the thickness of the substance) can be obtained by equation (8) below. Based on equation (8), the planar distribution obtaining unit 112 performs the iterative calculation using, as the initial value, the value of the planar distribution when it is assumed that noise is absent.

$$d_1 = f^{-1}(I) \quad (8)$$

As another initial value setting method, an image obtained by performing image processing for the image obtained by equation (8) can be input as the initial value of the thickness of the substance. Alternatively, using the energy subtraction method, a planar distribution concerning the substance may be calculated by a method of smoothing an output image (for example, a thickness image of a soft tissue or a thickness image of a bone part) obtained by separating a plurality of substances contained in a plurality of radiation images captured using different radiation energies, and the output may be input as the initial value. That is, the planar distribution obtaining unit 112 can perform the iterative calculation using, as the initial value, the value of the planar distribution obtained by the smoothing process for the output image.

The process from step S304 is the process of the iterative calculation (sequential approximation). The planar distribution obtaining unit 112 repeats updating the sequential approximation solution in equation (7) in step S305 until reaching a preset iterative count n (YES in step S304). In the sequential approximation solution updating process, the process of the differential term (grad) in equation (7) may be obtained numerically or analytically. Details of the processing method of the differential term (grad) will be described later.

In step S306, the planar distribution obtaining unit 112 updates a coefficient an representing the speed of iteration. In general, since the difference should be large in solutions in first few times of iteration as compared to a final solution, the planar distribution obtaining unit 112 sets the coefficient $\alpha_n$ representing the speed of iteration to a large value (first coefficient value). Since the error should become less as the iterative calculation progresses, the planar distribution obtaining unit 112 sets the coefficient an representing the speed of iteration to a smaller value, that is, a second coefficient value less than the first coefficient value. The coefficient an representing the speed of iteration has a form of, for example, $k \times \alpha_n \to \alpha_{n+1}$. Here, "→" means that $k \times \alpha_n$ is substituted into $\alpha_{n+1}$. The coefficient k is a constant of a real number greater than zero and less than one (0<k (constant of real number)<1). If the first coefficient value is an, the second coefficient value ($\alpha_{n+1}$) can be obtained by k×first coefficient value. The planar distribution obtaining unit 112 updates the setting of the coefficient an such that the coefficient an representing the speed of iteration becomes small in accordance with the iteration count of the iterative calculation (sequential approximation).

If the iteration count has reached the set iteration count n in the determination process of step S304 (NO in step S304), the planar distribution obtaining unit 112 ends the process.
(Example of Process Using Detailed Equations)
(Relationship f(d) Between Thickness of Substance and Image (Output Image))

An example of a process using detailed equations will be described next. First, as for the relationship f(d) between the thickness of a substance and an image (output image) appearing in equation (1), equation (2), and the like, an equation of the Beer-Lambert law concerning transmission shown by equation (9) or equation (10) can be used. In equation (9) and equation (10), $I'/I_0$ is the attenuation factor, μ is the ray attenuation coefficient, d is the thickness of the substance, E is the energy of radiation, and Φ(E) indicates the spectrum of radiation. I is the input image, and indicates images (a low-energy radiation image and a high-energy radiation image) captured using two different radiation energies. When the two independent simultaneous equations are solved, the values of thicknesses $d_1$ and $d_2$ of substance, which are unknown variables, can be obtained.

$$\frac{I'}{I_0} = I = f(d) = \lambda(d) = \frac{\int_0^\infty \Phi(E) E \exp\{-\mu_1(E)d_1 - \mu_2(E)d_2\} dE}{\int_0^\infty \Phi(E) E dE} \quad (9)$$

$$\frac{I'}{I_0} = I = f(d) = \lambda(d) = \frac{\sum_E \Phi(E) E \exp\{-\mu_1(E)d_1 - \mu_2(E)d_2\}}{\sum_E \Phi(E) E} \quad (10)$$

(Term of Likelihood in Equation (6))

The term of a likelihood representing the probability that an image corresponding to an input becomes an input image when the input value is the value of a planar distribution (the thickness d of a substance) will be described. The planar distribution obtaining unit 112 uses a normal distribution or a Poisson distribution as the probability distribution of likelihood.

As for the likelihood (log p(I|d): equation (6)) representing the probability that the image is I for the thickness d of the substance, equation (11) below, which approximates the probability distribution by a normal distribution, or equation (12) below, which approximates the probability distribution by a Poisson distribution can be used. Here, in equation (11), σ indicates variance. Also, in equation (12), the probability that an event occurs $\lambda_1$ times on average during a predetermined time occurs $k_1$ times (k is a positive integer) and the probability that an event occurs $k_2$ times occurs $k_2$ times (k is a positive integer) are indicated, and the probability that $I = k_1$ holds and the probability that $I_2 = k_2$ holds are independent.

$$p(I \mid d) = \frac{1}{\sqrt{2\pi\sigma_1^2\sigma_2^2}} \exp\left\{-\frac{(I_1 - f_1(d))^2}{2\sigma_1^2}\right\} \exp\left\{-\frac{(I_2 - f_2(d))^2}{2\sigma_2^2}\right\} \quad (11)$$

$$p(I_1 = k_1, I_2 = k_2 \mid d) = \frac{\lambda_1(d)^{k_1} \lambda_2(d)^{k_2} \exp(-\lambda_1(d) - \lambda_2(d))}{k_1! k_2!} \quad (12)$$

(Term of Prior Probability in Equation (6))

The planar distribution obtaining unit 112 receives, as an input image, a plurality of radiation images captured using different radiation energies, obtains an output image representing a planar distribution for a substance contained in the input image, and evaluates the continuity of the planar distribution based on the difference between the pixel value of a pixel of interest and the pixel value of a peripheral pixel in the output image.

A prior probability concerning continuity in the output image is obtained based on the evaluation of the continuity of the planar distribution. As for the term (log $p_{prior}$(d)) of prior probability shown in equation (6), for example, a term that compares (difference) between the pixel of interest and the peripheral pixel can be introduced. As an example, for example, equation (13) below can be used as the term of prior probability. Here, the planar distribution obtaining unit 112 obtains the prior probability based on the difference between the pixel value of a pixel of interest in the output image and the pixel value of a peripheral pixel with respect to the pixel of interest.

$$\log p_{prior}(d_{1i,j}, d_{2i,j}) = \quad (13)$$
$$\sum_{k,l} \left[ -\mu_1 |d_{1i,j} - d_{1i+k,\ j+l}| - \eta_1 (d_{1i,j} - d_{1i+k,\ j+l})^2 - \right.$$
$$\left. \mu_2 |d_{2i,j} - d_{2i+k,\ j+l}| - \eta_2 (d_{2i,j} - d_{2i+k,\ j+l})^2 \right]$$

In equation (13), represents an absolute value. In equation (13), each of k and l is a suffix used to express the term of an adjacent pixel in the up-and-down, left-and-right, and diagonal directions with respect to the pixel of interest, and as an example, a combination of k=±1 and l=±1 can be used. The range of comparison (difference) is not limited to adjacent pixels, and a term of comparison (difference) with a peripheral pixel in a wider range including the adjacent pixels of the combination of k=±1 and l=±1 can be added to the term of prior probability in equation (13).

When the term (regularization term) of prior probability as shown in equation (13) is introduced, the planar distribution obtaining unit 112 can evaluate the spatial continuity of the planar distribution in the output image based on comparison (difference) between the pixel value of the pixel of interest and the pixel value of the peripheral pixel in the output image (substance separation image). Then, the planar distribution obtaining unit 112 performs a noise reduction process for the output image based on the evaluation result of the spatial continuity of the planar distribution. This can reduce probabilistically distributed noise and obtain an image of higher image quality.

Figure 4:
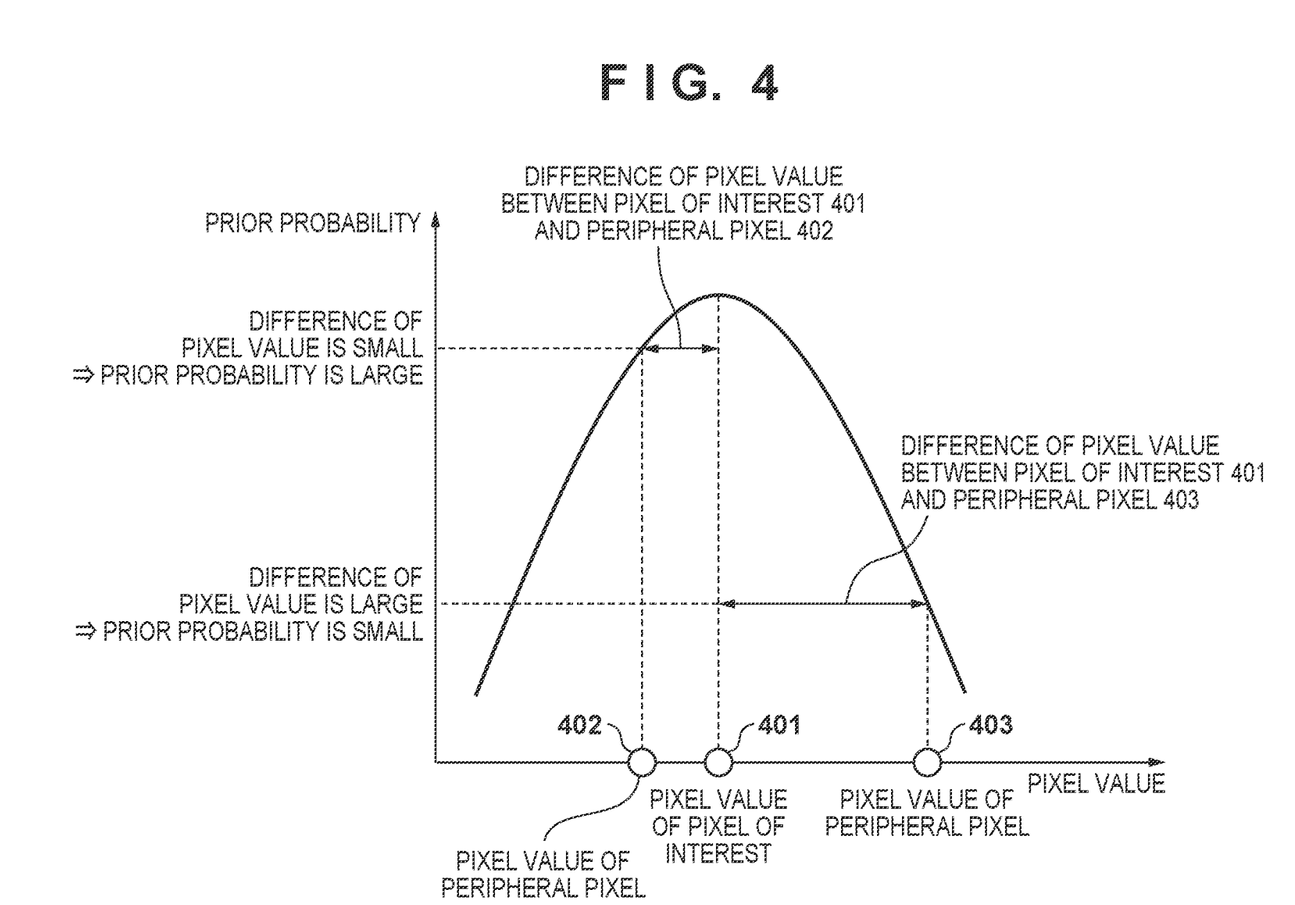
FIG. 4 is a view schematically showing the differences between pixel values and the distribution of prior probability.

Regularization coefficients $\mu_i$ and $\eta_i$ in the term (regularization term) of prior probability as shown in equation (13) are coefficients representing the degree (strength) of the influence of the term (regularization term) of prior probability. The greater the values the regularization coefficients pi and qi take are, the stronger the influence of the assumption introduced by the prior probability is. FIG. 4 is a view schematically showing the differences between pixel values and the distribution of prior probability. If the difference between pixel values is small, as indicated by a pixel 401 of interest and a peripheral pixel 402, the prior probability exhibits a tendency of becoming large. On the other hand, if the difference between pixel values is large, as indicated by the pixel 401 of interest and a peripheral pixel 403, the prior probability exhibits a tendency of becoming small.

That is, the term (regularization term) in equation (13) means that the smaller the evaluation value of continuity (the difference between the pixel value of the pixel of interest and the pixel value of the peripheral pixel) is, the higher the prior probability is.

In addition, when large values are set for the regularization coefficients pi and qi, the output of the term (regularization term) of prior probability can be made large. Accordingly, the assumption (a prior assumption that the output image is smooth because of the continuity of pixel values) introduced by the prior probability has a large influence. The greater the values of the regularization coefficients pi and qi are, the lesser the pixel value difference between the pixel of interest and the peripheral pixel is made by the output image obtaining calculation process (sequential approximation operation), and the smoother the obtained output image (substance separation image) becomes. Since there is a tendency of obtaining a smooth output image, noise in the planar distribution concerning the substance (the substance separation image representing the distribution of the thickness of the substance) can be reduced by using the term (regularization term) of prior probability.

The planar distribution obtaining unit 112 can change the regularization coefficients pi and qi representing the degree (strength) of the influence of the term (regularization term) of prior probability based on imaging conditions included in the prior information obtained by the prior information obtaining unit 111. For example, if the radiation irradiation condition (dose) is smaller than a predetermined threshold, the planar distribution obtaining unit 112 can change the regularization coefficients pi and qi to values larger than predetermined reference values to make the term (regularization term) of prior probability large, thereby doing a setting with priority on noise removal (noise reduction).

The planar distribution obtaining unit 112 can obtain information concerning the radiation irradiation condition (dose) based on the prior information obtained by the prior information obtaining unit 111. For example, tube information (a tube voltage, a tube current, and an irradiation time) included in the prior information is information concerning the dose, and the planar distribution obtaining unit 112 can change the regularization coefficients pi and qi representing the degree of the influence of the term (regularization term) of prior probability based on the radiation irradiation condition (dose). Note that if an adjusting device configured to adjust image quality is attached to the input device 114 of the radiation imaging apparatus 100, the planar distribution obtaining unit 112 can adjust the setting of the regularization coefficients $\mu_i$ and $\eta_i$ of the term (regularization term) of prior probability based on a value indicated by the adjusting device.

Subject information (height, weight, and the like) included in the prior information is information concerning the body shape of the subject, and is also information concerning the dose. Based on the subject information (information concerning the body shape of the subject) as information concerning the radiation irradiation condition (dose), the planar distribution obtaining unit 112 can change the regularization coefficients $\mu_i$ and $\eta_i$ representing the degree of the influence of the term (regularization term) of prior probability. For example, since the transmission dose becomes low as the weight of the subject become large, the planar distribution obtaining unit 112 can change the regularization coefficients pi and qi to values larger than predetermined reference values to make the term (regularization term) of prior probability large, thereby doing a setting with priority on noise removal (noise reduction).

The information of position setting of the C-arm 116 or the gantry 117 is also information concerning the dose. For example, if the distance to pass the radiation through the subject 102 is long because of the position or angle of the C-arm 116, that is, the relative position or angle between the radiation generation apparatus (radiation tube 101) and the radiation detection unit (FPD 103), the transmission dose is expected to be relatively low as compared to a case in which the distance is short. In addition, if the distance to pass the radiation through the subject is short, the transmission dose is expected to be relatively high as compared to a case in which the distance is long.

Based on the relative position or angle between the radiation generation apparatus (radiation tube 101) and the radiation detection unit (FPD 103) as information concerning the radiation irradiation condition (dose), the planar distribution obtaining unit 112 can change the regularization coefficients pi and qi representing the degree of the influence of the term (regularization term) of prior probability.

In addition, since the gantry 117 is one of the elements that shield radiation, the presence/absence of the gantry 117 is also information concerning the dose. Based on the information of the gantry 117 as information concerning the radiation irradiation condition (dose), the planar distribution obtaining unit 112 can change the regularization coefficients $\mu_i$ and $\eta_i$ representing the degree of the influence of the term (regularization term) of prior probability.

The present inventor found that introducing the term (regularization term) of prior probability to, of substance separation images, an image (thickness image) representing the distribution of the thickness of a substance concerning a soft tissue such as fat is effective for image quality improvement such as noise reduction. For this reason, if the part of interest is a soft tissue such as fat, the regularization coefficients of the term (regularization term) of prior probability for a thickness image concerning the soft tissue is set larger than the regularization coefficients of the term (regularization term) of prior probability for a thickness image concerning a hard tissue such as a bone to make the term (regularization term) of prior probability large. This can provide an image (substance separation image) of higher image quality in which noise is removed (noise is reduced).

In this case, the planar distribution obtaining unit 112 evaluates continuity in the thickness image of the soft tissue based on the difference between the pixel value of the pixel of interest and the pixel value of a peripheral pixel in the thickness image of the soft tissue. Based on the evaluation result of the spatial continuity of the planar distribution, the planar distribution obtaining unit 112 performs a noise reduction process for the output image. This can reduce probabilistically distributed noise and obtain an image of higher image quality.

Note that, if the part of interest is a hard tissue such as a bone, the regularization coefficients of the term (regularization term) of prior probability for a thickness image concerning the hard tissue such as a bone may be set greater than the regularization coefficients of the term (regularization term) of prior probability for a thickness image concerning a soft tissue such as fat.

When solving equation (13), in the steepest descent method, the differential concerning the thickness of the term (regularization term) of prior probability is calculated. If equation (13) is differentiated, two terms in equation (13), which are given by equation (14) and equation (15) below, are discontinuous solutions.

$$-\mu_1 |d_{1i,j} - d_{1i+k,j+l}| \tag{14}$$

$$-\mu_2 |d_{2i,j} - d_{2i+k,j+l}| \tag{15}$$

The two terms given by equation (14) and equation (15) can specifically be expressed as $$-\mu_1 \operatorname{sign}(d_{1i,j} - d_{1i+k,j+l}), -\mu_2 \operatorname{sign}(d_{2i,j} - d_{2i+k,j+l})(\operatorname{sign}(x) = +1(x \geq 0), -1(x < 0)) \tag{16}$$

To avoid the discontinuity in equation (14) and equation (15), the integral of the function of equation (17) below, which includes a function whose differential is continuous, for example, a sigmoid function, is used in place of a term including an absolute value, that is, in place of the term given by equation (14), thereby avoiding the discontinuity.

$$-\mu_1 \left( \frac{2}{1 + e^{-k(d_{1i,j} - d_{1i+k,j+1})}} - 1 \right) \tag{17}$$

An example in which the term (regularization term) of prior probability has the term of the difference between the pixel of interest and the peripheral pixel (for example, equation (13)) has been described above. However, the term (regularization term) of prior probability is not necessarily the difference between the pixel of interest and the peripheral pixel. The planar distribution obtaining unit 112 can also obtain the prior probability based on the pixel value of the pixel of interest in the output image (substance thickness image). For example, since the substance thickness image ($d_1$ or $d_2$) has a finite value of zero or more, a regularization term as shown by equation (18) below can be introduced using the thickness of the substance as the input. In equation (18), $\kappa$ is a positive constant, and is an example of a regularization coefficient.

$$\log p_{prior}(d_{1i,j}, d_{2i,j}) = h(d_{1i,j}) + h(d_{2i,j}) \tag{18}$$

$$h(d_{ni,j}) = \begin{cases} 0 & (d_{ni,j} \geq 0) \\ -\kappa_n d_{ni,j}^2 & (d_{ni,j} < 0) \end{cases}$$

When the thickness of a substance becomes less than zero, $\log_{prior}(d_{1i,j}, d_{2i,j})$ that is the term (regularization term) of prior probability shown in equation (18) also becomes less than zero. Hence, the entire posterior probability including the likelihood and the term (regularization term) of prior probability becomes small. The possibility that the substance thickness image ($d_1$ or $d_2$) becomes an image having a pixel value greater than zero improves. This prior probability also has an effect of causing the thickness image that should vary to positive and negative values to have only positive values, and is, therefore, an example of a term for evaluating the continuity of the planar distribution, like the term (regularization term) of prior probability, which has the term of the difference to a pixel on the periphery, and also provides an effect of reducing noise. That is, the planar distribution obtaining unit 112 evaluates the continuity of the planar distribution based on the pixel value of the pixel of interest in the output image (substance thickness image), and reduces noise in the output image based on the evaluation result. This can reduce probabilistically distributed noise and obtain an image of higher image quality.

(Speedup of Process)

When equation (1) and equation (8) to equation (13) are substituted into equation (7), the sequential approximation solution (updating solution) of equation (7) can be obtained. When the equation is rewritten, an analysis solution can be obtained, and as a result, the operation can further be speeded up.

Equation (11) is an equation that approximates, by a normal distribution, the probability distribution of likelihood representing the probability that the image is I when the thickness of the substance is d. When the logarithm of equation (11) is calculated, equation (11) can be expressed as:

$$\log p(I \mid d) = -\frac{1}{2} \log 2\pi \sigma_1^2 - \frac{1}{2} \log 2\pi \sigma_2^2 - \frac{(I_1 - f_1(d))^2}{2\sigma_1^2} - \frac{(I_2 - f_2(d))^2}{2\sigma_2^2} \tag{19}$$

The likelihood can be expanded as shown by equation (19), and the term (regularization term) of prior probability can be expanded as shown by equation (13). Hence, the equation portion $-\log p(I|d) - \log p_{prior}(d)$ in equation (7) can be expressed as:

$$-\log p(I \mid d) - \log p_{prior}(d) = \frac{1}{2} \log 2\pi \sigma_1^2 + \frac{1}{2} \log 2\pi \sigma_2^2 + \frac{(I_1 - f_1(d))^2}{2\sigma_1^2} + \frac{(I_2 - f_2(d))^2}{2\sigma_2^2} - \sum_{k,l} [-\mu_1 |d_{1i,j} - d_{1i+k, j+l}| - \eta_1 (d_{1i,j} - d_{1i+k, j+l})^2 - \mu_2 |d_{2i,j} - d_{2i+k, j+l}| - \eta_2 (d_{2i,j} - d_{2i+k, j+l})^2] \tag{20}$$

When equation (20) is substituted into equation (7), the term of grad representing the differential (gradient) of a vector can be expressed as:

$$grad(-\log p_{post}(d \mid I)) = \begin{pmatrix} \dfrac{\partial}{\partial d_{1i,j}}(-\log p_{post}(d \mid I)) \\ \dfrac{\partial}{\partial d_{2i,j}}(-\log p_{post}(d \mid I)) \end{pmatrix} = \quad (21)$$

$$\begin{pmatrix} \dfrac{I_1 - f_1(d)}{\sigma_1^2}\dfrac{\partial[I_1-f_1(d)]}{\partial d_{1i,j}} + \dfrac{I_2-f_2(d)}{\sigma_2^2}\dfrac{\partial[I_2-f_2(d)]}{\partial d_{1i,j}} - \\ \sum_{k,l}[-\mu_1\mathrm{sign}(d_{1i,j}-d_{1i+k,\,j+1}) - 2\eta_1(d_{1i,j}-d_{1i+k,\,j+1})] \\ \dfrac{I_1 - f_1(d)}{\sigma_1^2}\dfrac{\partial[I_1-f_1(d)]}{\partial d_{2i,j}} + \dfrac{I_2-f_2(d)}{\sigma_2^2}\dfrac{\partial[I_2-f_2(d)]}{\partial d_{2i,j}} - \\ \sum_{k,l}[-\mu_2\mathrm{sign}(d_{2i,j}-d_{2i+k,\,j+1}) - 2\eta_2(d_{2i,j}-d_{2i+k,\,j+1})] \end{pmatrix}$$

By analytically obtaining the solution of equation (21), the arithmetic process can further be speeded up while maintaining the operation accuracy.

Equation (12) is an equation that approximates the probability distribution of likelihood by a Poisson distribution. When the logarithm of equation (12) is calculated, equation (12) can be expressed as:

$$\log p(I\mid d) = k_1 \log \lambda_1(d) + k_2 \log \lambda_2(d) - \lambda_1(d) - \lambda_2(d) - \log k_1! - \log k_2! \quad (22)$$

The likelihood can be expanded as shown by equation (22), and the term (regularization term) of prior probability can be expanded as shown by equation (13). Hence, the equation portion $-\log p(I\mid d) - \log p_{prior}(d)$ in equation (7) can be expressed as:

$$-\log p(I \mid d) = \quad (23)$$

$$-\log p_{prior}(d) = -k_1 \log \lambda_1(d) - k_2 \log \lambda_2(d) + \lambda_1(d) + \lambda_2(d) + \log k_1! +$$

$$\log k_2! - \sum_{k,l}\left[-\mu_1|d_{1i,j}-d_{1i+k,\,j+l}| - \eta_1(d_{1i,j}-d_{1i+k,\,j+l})^2 - \right.$$

$$\left. \mu_2|d_{2i,j}-d_{2i+k,\,j+l}| - \eta_2(d_{2i,j}-d_{2i+k,\,j+l})^2\right]$$

When equation (23) is substituted into equation (7), the term of grad representing the differential (gradient) of a vector can be expressed as:

$$grad(-\log p_{post}(d \mid I)) = \begin{pmatrix} \dfrac{\partial}{\partial d_{1i,j}}(-\log p_{post}(d \mid I)) \\ \dfrac{\partial}{\partial d_{2i,j}}(-\log p_{post}(d \mid I)) \end{pmatrix} = \quad (24)$$

$$\begin{pmatrix} -\dfrac{k_1}{\lambda_1(d)}\dfrac{\partial \lambda_1(d)}{\partial d_{1i,j}} - \dfrac{k_2}{\lambda_2(d)}\dfrac{\partial \lambda_2(d)}{\partial d_{1i,j}} + \dfrac{\partial \lambda_1(d)}{\partial d_{1i,j}} + \dfrac{\partial \lambda_2(d)}{\partial d_{1i,j}} - \\ \sum_{k,l}[-\mu_1\mathrm{sign}(d_{1i,j}-d_{1i+k,\,j+1}) - 2\eta_1(d_{1i,j}-d_{1i+k,\,j+1})] \\ -\dfrac{k_1}{\lambda_1(d)}\dfrac{\partial \lambda_1(d)}{\partial d_{2i,j}} - \dfrac{k_2}{\lambda_2(d)}\dfrac{\partial \lambda_2(d)}{\partial d_{2i,j}} + \dfrac{\partial \lambda_1(d)}{\partial d_{2i,j}} + \dfrac{\partial \lambda_2(d)}{\partial d_{2i,j}} - \\ \sum_{k,l}[-\mu_2\mathrm{sign}(d_{2i,j}-d_{2i+k,\,j+1}) - 2\eta_2(d_{2i,j}-d_{2i+k,\,j+1})] \end{pmatrix}$$

By analytically obtaining the solution of equation (24), the arithmetic process can further be speeded up while maintaining the operation accuracy.

(Single Color Approximation)

$f_i(d)$ appearing in equation (11) that approximates the probability distribution of likelihood by a normal distribution or $\lambda_i(d)$ (i=1, 2) appearing in equation (12) that approximates the probability distribution of likelihood by a Poisson distribution is an average pixel value. This is an average pixel value in the absence of noise and can be decided based on equation (9). When equation (9) or equation (10) is substituted into equation (21) or equation (24), a sequential approximation solution by the steepest descent method can be obtained from equation (7). By considering the width of a radiation spectrum ($\Phi(E)$) in equation (9) and equation (10), the influence (beam hardening) of an energy change at the time of radiation transmission can be suppressed.

On the other hand, when single color approximation is performed for the radiation spectrum using a delta function (e=1, 2), as indicated by equation (25) below, a solution can be expressed more easily. If calculation accuracy is necessary, the calculation is performed using equation (9) or equation (10). If a calculation speed is necessary, the calculation is performed by introducing single color approximation to the radiation spectrum ($\Phi(E)$) in equation (9) or equation (10). The planar distribution obtaining unit 112 approximates radiation spectra corresponding to different radiation energies as a radiation spectrum of a single color, thereby obtaining an output image.

$$\Phi(E) = N\delta(E - E_e) \quad (25)$$

When single color approximation is introduced, equation (9) or equation (10) becomes equation (26) below. When the coordinates of the thickness d of a substance are also taken into consideration, equation (26) can be expressed as equation (27).

$$f_e(d) = \lambda_e(d) = \exp\{-\mu_1(E_e)d_1 - \mu_2(E_e)d_2\} \quad (26)$$

$$f_e(d_{i,j}) = \lambda_e(d_{i,j}) = \exp\{-\mu_1(E_e)d_{1i,j} - \mu_2(E_e)d_{2i,j}\} \quad (27)$$

When differentiated, equation (27) can be expressed as equation (28) or equation (29).

$$\dfrac{\partial f(d_{i,j})}{\partial d_{1i,j}} = \dfrac{\partial \lambda(d_{i,j})}{\partial d_{1i,j}} = -\mu_1(E_e)\exp\{-\mu_1(E_e)d_{1i,j} - \mu_2(E_e)d_{2i,j}\} \quad (28)$$

$$\dfrac{\partial f(d_{i,j})}{\partial d_{2i,j}} = \dfrac{\partial \lambda(d_{i,j})}{\partial d_{2i,j}} = -\mu_2(E_e)\exp\{-\mu_1(E_e)d_{1i,j} - \mu_2(E_e)d_{2i,j}\} \quad (29)$$

When equation (27), equation (28), and equation (29) are substituted into equation (21) concerning the normal distribution, the components of equation (21) can be expressed as equation (30) and equation (31) below.

$$\dfrac{\partial}{\partial d_{1i,j}}(-\log p_{post}(d \mid I)) = \quad (30)$$

$$\dfrac{I_1 - e^{-\mu_1(E_1)d_{1i,j} - \mu_2(E_1)d_{2i,j}}}{\sigma_1^2}\mu_1(E_1)e^{-\mu_1(E_1)d_{1i,j} - \mu_2(E_1)d_{2i,j}} +$$

$$\dfrac{I_2 - e^{-\mu_1(E_2)d_{1i,j} - \mu_2(E_2)d_{2i,j}}}{\sigma_2^2}\mu_1(E_2)e^{-\mu_1(E_2)d_{1i,j} - \mu_2(E_2)d_{2i,j}} -$$

$$\sum_{k,l}[-\mu_1 \mathrm{sign}(d_{1i,j}-d_{1i+k,\,j+l}) - 2\eta_1(d_{1i,j}-d_{1i+k,\,j+l})]$$

$$\dfrac{\partial}{\partial d_{2i,j}}(-\log p_{post}(d \mid I)) = \quad (31)$$

$$\dfrac{I_1 - e^{-\mu_1(E_1)d_{1i,j} - \mu_2(E_1)d_{2i,j}}}{\sigma_1^2}\mu_2(E_1)e^{-\mu_1(E_1)d_{1i,j} - \mu_2(E_1)d_{2i,j}} +$$

-continued $$\frac{I_2 - e^{-\mu_1(E_2)d_{1i,j} - \mu_2(E_2)d_{2i,j}}}{\sigma_2^2} \mu_2(E_2)e^{-\mu_1(E_2)d_{1i,j} - \mu_2(E_2)d_{2i,j}} - $$

$$\sum_{k,l}[-\mu_2 \text{sign}(d_{2i,j} - d_{2i+k, j+l}) - 2\eta_2(d_{2i,j} - d_{2i+k, j+l})]$$

Similarly, when equation (27), equation (28), and equation (29) are substituted into equation (24) concerning the Poisson distribution, the components of equation (24) concerning the Poisson distribution in a case in which single color approximation is introduced can be obtained. Note that single color approximation of a radiation spectrum has been described here. However, when the reproducibility of a normal distribution or a Poisson distribution, that is, the fact that when independent probability variables $X_1$ and $X_2$ comply with a normal distribution or a Poisson distribution (parameters $\lambda_1$ and $\lambda_2$), the sum $(X_1+X_2)$ of the probability variables also complies with the normal distribution or the Poisson distribution is taken into consideration, a similar argument can be made even for a pixel value $I=\Sigma_i i(E_i)$ when the width of the radiation spectrum is taken into consideration. In this case, the planar distribution obtaining unit 112 can obtain an output image by adding the pixel values of images obtained based on radiation spectra corresponding to different radiation energies and apply the process according to this embodiment to the obtained output image.

According to the present invention, it is possible to reduce noise and to obtain an image of higher image quality.

OTHER EMBODIMENTS

Embodiment(s) of the present invention can also be realized by a computer of a system or an apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., an application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., a central processing unit (CPU), or a micro processing unit (MPU)) and may include a network of separate computers or separate processors to read out and to execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), a digital versatile disc (DVD), or a Blu-ray Disc (BD)™) a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
a planar distribution obtaining unit configured, using a plurality of radiation images captured using different radiation energies as input images, to obtain, by a sequential approximation solution by an iterative calculation, an output image representing a planar distribution for a substance contained in the input image,
wherein, based on a likelihood and a prior probability using one of a pixel value of a pixel of interest or a pixel value of a peripheral pixel as an input, the planar distribution obtaining unit decides the output image such that a probability that an output is a value of the planar distribution when an input is the input image that is maximized.

2. The image processing apparatus according to claim 1, wherein the planar distribution obtaining unit obtains the prior probability based on a difference between the pixel value of the pixel of interest and the pixel value of the peripheral pixel in the output image.

3. The image processing apparatus according to claim 1, wherein the planar distribution obtaining unit obtains the prior probability based on the pixel value of the pixel of interest in the output image.

4. The image processing apparatus according to claim 2, wherein the planar distribution obtaining unit evaluates continuity of the planar distribution by the difference, and reduces noise in the output image based on the evaluation.

5. The image processing apparatus according to claim 1, wherein, in accordance with an iteration count of the iterative calculation, the planar distribution obtaining unit updates a setting of a coefficient representing a speed of iteration such that the coefficient becomes small.

6. The image processing apparatus according to claim 1, wherein the planar distribution obtaining unit performs the iterative calculation using, as an initial value, a value of a planar distribution in a case in which noise is assumed to be absent.

7. The image processing apparatus according to claim 1, wherein the planar distribution obtaining unit performs the iterative calculation using, as an initial value, a value of a planar distribution obtained by a smoothing process for the output image.

8. The image processing apparatus according to claim 1, wherein the planar distribution obtaining unit obtains the output image by adding pixel values of images obtained based on radiation spectra corresponding to the different radiation energies.

9. The image processing apparatus according to claim 1, wherein the planar distribution obtaining unit obtains the output image by approximating radiation spectra corresponding to the different radiation energies as a radiation spectrum of a single color.

10. The image processing apparatus according to claim 1, wherein the planar distribution obtaining unit uses one of a normal distribution and a Poisson distribution as a probability distribution of the likelihood.

11. The image processing apparatus according to claim 1, wherein the planar distribution obtaining unit obtains, as the output image, an image separated to each of a plurality of substances contained in the plurality of radiation images.

12. The image processing apparatus according to claim 11, wherein the planar distribution obtaining unit obtains, as the output image, each of a thickness image of a soft tissue that constitutes a subject and a thickness image of a hard tissue that constitutes the subject.

13. The image processing apparatus according to claim 12, wherein the planar distribution obtaining unit evaluates continuity in the thickness image of the soft tissue based on a difference between a pixel value of a pixel of interest and a pixel value of a peripheral pixel in the thickness image of the soft tissue.

14. The image processing apparatus according to claim 1, wherein the planar distribution obtaining unit changes a regularization coefficient representing a degree of an influence of the prior probability based on an imaging condition.

15. The image processing apparatus according to claim 1, wherein the planar distribution obtaining unit changes a regularization coefficient representing a degree of an influence of the prior probability based on a radiation irradiation condition.

16. The image processing apparatus according to claim 1, wherein the planar distribution obtaining unit changes a regularization coefficient representing a degree of an influence of the prior probability based on information concerning a body shape of a subject.

17. An image processing method comprising:
using a plurality of radiation images captured using different radiation energies as input images; and
obtaining, by a sequential approximation solution by an iterative calculation, an output image representing a planar distribution for a substance contained in the image,
wherein, based on a likelihood and a prior probability using one of a pixel value of a pixel of interest or a pixel value of a peripheral pixel as an input, in the obtaining, the output image is decided such that a probability that an output is a value of the planar distribution when an input is the input image that is maximized.

18. A non-transitory computer-readable storage medium storing a program configured to cause a computer to execute the method according to claim 17.

19. An image processing apparatus comprising:
a planar distribution obtaining unit configured, using a plurality of radiation images captured using different radiation energies as input images, to obtain an output image representing a planar distribution for a substance contained in the input image,
wherein, based on a likelihood and a prior probability using one of a pixel value of a pixel of interest or a pixel value of a peripheral pixel as an input, the planar distribution obtaining unit decides the output image such that a probability that an output is a value of the planar distribution when an input is the input image that is maximized, the planar distribution obtaining unit obtains:
the output image by adding pixel values of images obtained based on radiation spectra corresponding to the different radiation energies, or
the output image by approximating radiation spectra corresponding to the different radiation energies as a radiation spectrum of a single color.

* * * * *